United States Patent
Dourdeville

(10) Patent No.: US 6,404,193 B1
(45) Date of Patent: Jun. 11, 2002

(54) SOLVENT SUSCEPTIBILITY COMPENSATION FOR COUPLED LC-NMR

(75) Inventor: Theodore A. Dourdeville, Marion, MA (US)

(73) Assignee: Waters Investments Limited ( * ) Notice: Subject to any disclaimer, the term of this patent is extended or adjusted under 35 U.S.C. 154(b) by 0 days.

(21) Appl. No.: 09/829,064

(22) Filed: Apr. 9, 2001

(51) Int. Cl.[7] .................................................. G01V 3/00
(52) U.S. Cl. ........................ 324/306; 324/307; 324/308; 324/309; 324/318; 324/321
(58) Field of Search ................................. 324/306, 308, 324/307, 309, 310, 316, 317, 318, 321

(56) References Cited

U.S. PATENT DOCUMENTS

| | | | | |
|---|---|---|---|---|
| 5,221,903 A | * | 6/1993 | Kasten et al. | 324/318 |
| 5,278,501 A | * | 1/1994 | Guilfoyle | 324/300 |
| 5,654,636 A | * | 8/1997 | Sweedler et al. | 324/307 |
| 5,684,401 A | * | 11/1997 | Peck et al. | 324/318 |
| 5,831,434 A | * | 11/1998 | Shigezane et al. | 324/321 |
| 5,867,026 A | * | 2/1999 | Haner | 324/321 |
| 5,986,453 A | * | 11/1999 | Anderson et al. | 324/300 |

* cited by examiner

*Primary Examiner*—Edward Lefkowitz
*Assistant Examiner*—Dixomara Vargas
(74) *Attorney, Agent, or Firm*—Brian Michaelis

(57) ABSTRACT

A method and apparatus in which the limitation upon analysis caused by variation of the magnetic susceptibility of the solvent conveying a sample to an NMR spectrometer can be addressed. The solvent composition which is used to bring about elution of analyte from devices such as chromatography columns can be varied without causing a corresponding variation of the solvent composition used to transport the analyte to the NMR spectrometer. The decoupling is achieved by the summing into the chromatographic stream, post column, a solvent composition which is complementary to the instantaneous composition emerging from the column, such that the magnetic susceptibility of the summed streams remains constant.

19 Claims, 2 Drawing Sheets

SOLVENT SUSCEPTIBILITY COMPENSATION FOR COUPLED LC-NMR

FIELD OF THE INVENTION

The present invention relates to the coupling of a liquid-phase analysis technique such as liquid chromatography with Nuclear Magnetic Resonance ("NMR") spectroscopy.

BACKGROUND OF THE INVENTION

The practice of modern high-resolution NMR spectroscopy on a sample dissolved or otherwise borne in a liquid phase requires that the uniformity of the applied static magnetic field ($B_0$) be maintained to the parts-per-billion level over the actively-interrogated sample region. Considerable effort has been expended over many years to minimize the contribution of sample probe hardware to $B_0$ field non-uniformity. For example, in U.S. Pat. No. 5,684,401, Peck et. al. teach the use of a susceptibility-matching medium to significantly reduce the $B_0$ distortion attributable to differences in the magnetic susceptibilities of the various materials (including air) which comprise, or which reside adjacent to, a microcoil flow cell. Magnetic susceptibility is a measure of the extent to which magnetization can be induced in a material when subjected to an externally applied magnetic field. Each component of the flow cell, as well as the solvent, has associated with it a magnetic susceptibility. The magnetic susceptibility of the solvent stream, which bears the sample, is one of the variables that can contribute to non-uniformity of the field in the immediate vicinity of the sample. Poor $B_0$ field uniformity results in broad and distorted NMR spectral lineshape, as disclosed in the Peck reference and in the literature cited therein.

In cases where a flow-through cell is used, but where there is substantially no change of solvent composition across the active sensing region of the flow cell, it is generally possible to "shim" the spectrometer to the extent that good quality NMR spectra are produced. As used, the term "shimming" refers to the superposition of secondary fields for the purpose of locally minimizing the non-uniformity of $B_0$ in the vicinity of the sample. However, in the event that a change of solvent composition is impressed across the probe, as would be the case in gradient elution liquid chromatography, a dramatic reduction in spectral quality can result. Typical liquid chromatography solvents as would be used in reverse phase gradient elution have magnetic susceptibilities which differ at the part-per-million level, whereas the desired $B_0$ uniformity is at the parts-per-billion level. In practice, it becomes apparent that solvent composition differences of relatively small magnitude (from a few per cent to less than one per cent), when impressed across the NMR detector cell volume, can result in demonstrably degraded NMR spectra, which may be rendered unusable for structure elucidation. This phenomenon dramatically diminishes the ability to utilize, for example, gradient-mode liquid chromatography to bring about sample focussing or other modes of sample manipulation, within a liquid inlet system to an NMR spectrometer.

Several approaches to solving the above-referenced problem have been attempted within the prior art. At least one commercial NMR spectrometer manufacturer offers a hardware accessory for use with conventional-scale liquid chromatography, which allows the collection of the HPLC eluent into a series of discrete loops. The contents of the individual loops are analyzed by the NMR spectrometer off-line from the chromatography in a separate sequence of analyses. Solvent compositional variations, which may exist over the length of a sample loop at the time of fluid capture, have an opportunity to diffuse toward equilibrium. At the time of the secondary analysis, the loop contents can be delivered into the NMR detection cell by a solvent of choice, which may be chosen to match the properties of the elution solvent at the time of a given sample's capture. Additionally, the loop volume and the detection cell volume may be chosen in such a way that the equilibrated loop contents overfill, or fully flush through, the interrogated volume of the detector cell.

There are several significant disadvantages of this approach. Most importantly, the NMR spectrometer is no longer on-line. The NMR analysis requires a separate and distinct set of processes to "re-play" the segmented chromatogram. The volume of the individual loops defines and limits the volumetric resolution of the chromatographic separation (i.e. the coarseness of the segmentation). At a defined loop volume, the number of loops available limits the overall volume of the chromatographic separation which is preserved.

If fluid transfer to the loop storage device is being steered "intelligently", as by an auxiliary detector such as a UV absorbance detector or a mass spectrometer, in order to selectively capture peaks of interest within a chromatogram, it becomes a requirement that the peaks of interest also be detectable by this alternate detection means. A compound of NMR interest, with no useable UV chromophore, would be undetectable by the UV detector and would therefore by-pass collection in this scheme. Similarly, a compound of NMR interest, for which ionization and analysis conditions were not properly pre-established at the mass spectrometer, would be undetectable by the mass spectrometer, and would also by-pass collection.

Additionally, disadvantageously the loop storage device requires the presence of a switching valve in-line with the chromatographic stream to direct the flow into the target loop. The presence of switching valve hardware can further degrade the fidelity of an eluting zone or band. Such degradation is particularly evident as the volume is reduced from a conventional chromatographic volume scale to a capillary chromatographic volume scale.

Other attempts to minimize the effect of solvent composition and susceptibility variation on NMR spectral quality, within the prior art, have been to limit the on-line operation to use with only extremely shallow compositional gradients. If the user-programmed time-rate-of-change of solvent composition is sufficiently shallow, then the resulting volume-rate-of-change of composition produced can be shallow enough that the compositional difference encompassed by the actively-interrogated volume of the NMR detection cell tends toward insignificance. In the case of an infinitely shallow gradient, there is substantially no compositional difference impressed across the cell, but correspondingly the liquid-phase separation is effectively isocratic (time-invariant).

Restricting LC-NMR operation to shallow composition gradients of typically 1 per cent composition change per minute or less, imposes significant limitations on the user. The analysis time becomes very lengthy if a large compositional range is to be spanned by the gradient. Compositional gradients are commonly employed to permit the separation and analysis of materials of widely differing retention behavior. A typical gradient profile may call for the percentage of a given solvent component to change by 40, 60 or even 100 percent, in order to allow elution of all of the analyte species present. If a large-percentage change is limited to occur at a rate less than or equal to 1 per cent per minute, then the analysis time may become unacceptably long.

Additionally, shallow gradients may not achieve the same sample focussing or concentrating behavior that a steeper gradient can provide. In certain modes of operation, a user may wish to introduce a sample, which resides at a dilute concentration in a relatively large volume of liquid. That sample may be focussed or concentrated on a chromatography column under an initial set of elution conditions where the analyte is strongly retained, and where the liquid in which the sample was initially dissolved is flushed through the column. The user may then apply a relatively steep compositional gradient to elute the material off of the column and into the spectrometer in a very highly concentrated band, in order to optimize detection. In such a mode of operation, the programmed gradient which is employed may have a time-rate-of-change of composition of many per cent per minute. The corresponding volume-rate-of-change of composition may be used to affect the overall volume in which the band elutes. A limitation requiring the use of shallow gradients impairs or inhibits the rapid use of this mode of operation.

Consequently there are numerous limitations associated with prior approaches to solve the problems caused by variation of the magnetic susceptibility of the solvent surrounding the sample subjected to NMR analysis.

SUMMARY OF INVENTION

The present invention provides a method in which the limitation upon analysis caused by variation of the magnetic susceptibility of the solvent incorporating a sample can be addressed.

According to the invention, solvent composition which is used to bring about elution of an analyte from a device such as a chromatography column, can be varied without causing a corresponding variation of the solvent composition used to transport the analyte to an NMR spectrometer. The analytical stream has summed therewith a solvent composition which is complementary to the instantaneous composition emerging from a liquid-phase separation or analysis, such that the composition of the final output stream remains constant. The method according to the invention, can be accomplished by either an open-loop approach where a time-programmed gradient is executed substantially simultaneously by two solvent gradient generation systems, or by a closed loop approach where the system actively senses a property of the solvent stream arriving at a sensing cell located downstream of the column or other analytical device, and modulates the output of the compensating pumps in order to maintain that measured solvent property substantially constant.

In the open loop method according to the invention, a first solvent gradient is applied to the sample injector and column to bring about a sample elution from the column. A secondary solvent gradient having a complementary composition to the first gradient is sent through a delay volume, which mimics the delay attributable to the presence of the sample injector, column, and optional chromatographic detector in the analytical side of the system. The solvent flow and composition produced by the second gradient generator is summed with the analytical flow in a low-band broadening tee geometry such as the Nano-Tee currently commercialized by Waters Corporation, of Milford Mass. The accuracy with which composition change produced within the analytical side of the system is nulled is a function of the inherent compositional accuracies of the two gradient generators and of the matching of the compositional delay characteristics of the analytical and the compensation flow paths.

In the closed loop method according to the invention, the need for matching the fluid circuit of the chromatographic or analytical path with analogous fluidic components in the compensation or secondary mobile phase delivery path is eliminated. The closed loop method instead actively senses a solvent property such as the instantaneous solvent composition at a sensing cell located downstream of the column. The system controller modulates the output of the compensating pumps in order to maintain the measured solvent property substantially constant.

Features of the invention include provisions that allow for the analysis to be performed on-line. This ability to conduct analysis on line allows analysis to be conducted without a separate and distinct set of processes to replay the segmented chromatogram. Moreover, the volumetric resolution of the chromatographic separation is not limited by a defined loop volume, nor is it necessary to include a switching valve that diminishes the fidelity of the eluting zone or band. Additionally, the analysis is not restricted to shallow gradients.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

Figure 1:
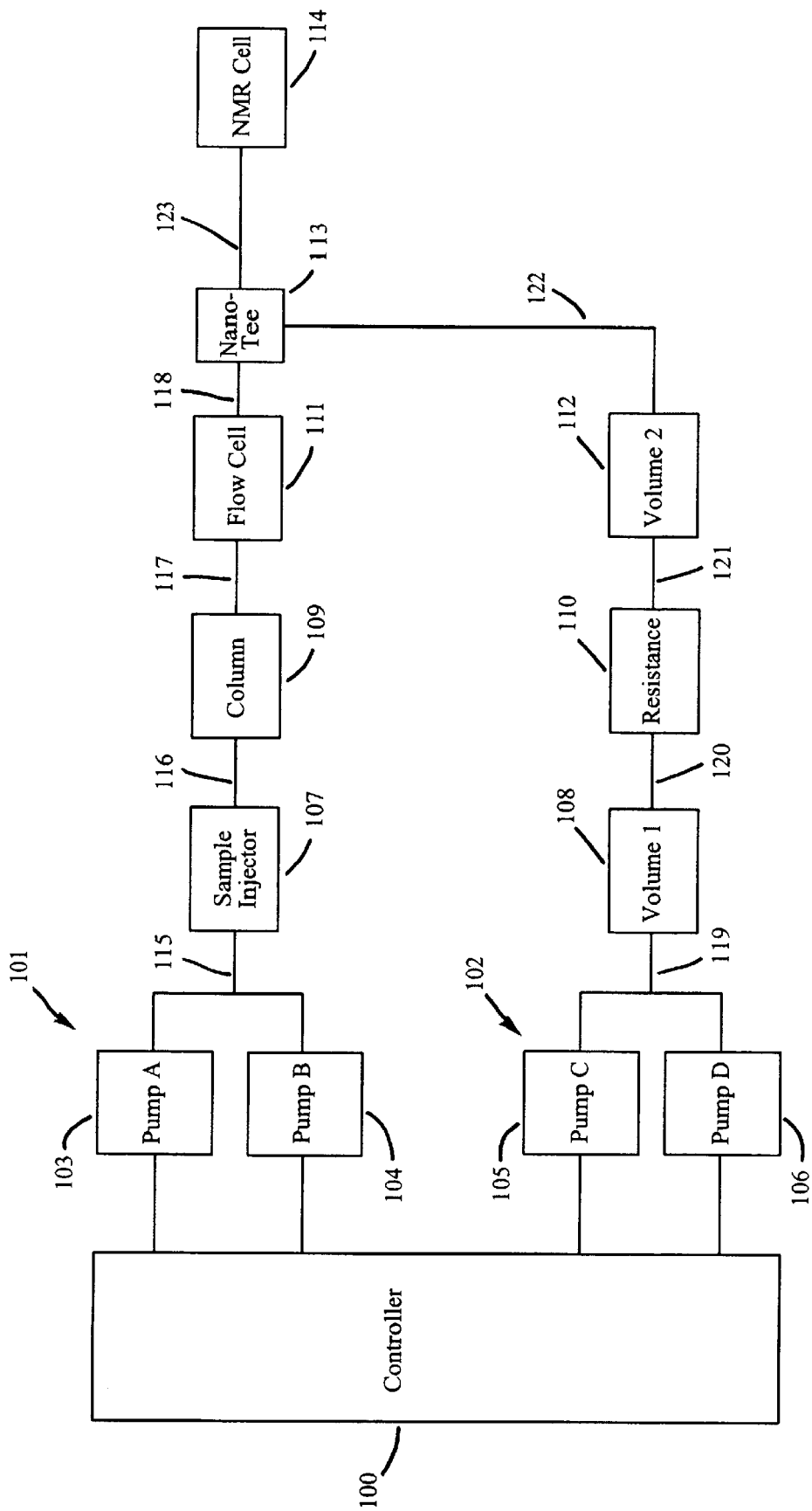
FIG. 1 shows a schematic drawing of a non-feedback or open-loop system of the present invention.

Referring in detail to the drawings, an open loop system according to the present invention is shown in FIG. 1. In the illustrative embodiment, a system controller 100, which in this illustrative embodiment is a microprocessor controller, is in communication with a first set of pumps 101 and a second set of pumps 102. The first set of pumps 101 has a first pump 103 and a second pump 104. The second set of pumps 102 has a first pump 105 and a second pump 106. A connecting tube 115 connects the first set of pumps 101 in fluidic communication with a sample injector 107. The injector 107 has a connecting tube 116 that causes the injector 107 to be in fluidic communication with a chromatography column 109. The chromatography column 109 has a connecting tube 117 that connects the chromatography column 109 in fluidic communication with a flow cell 111 associated with a conventional chromatography detector. The flow cell has a connecting tube 118 connecting the flow cell in fluidic communication with a nano-volume tee 113.

The second set of pumps 102 has a connecting tube 119 connecting the second set of pumps 102 in fluidic communication with a first volume 108. The first volume 108 has approximately the internal volume and flow characteristics of the injector 107. A connecting tube 120 connects the first volume 108 in fluidic communication with a resistance 110. The resistance 110 is configured to mimic the fluidic characteristics of the chromatography column 109. A connecting tube 121 causes the resistance 110 to be in fluidic communication with a second volume 112 which has approximately the internal volume and flow characteristics of the flow cell 111. A connecting tube 122 connects the second volume 112 in fluidic communication with the nano-volume tee 113. The nano-volume tee has a connecting tube 123 that causes the nano-volume tee 113 to be in fluidic communication with a NMR detection cell 114.

In the illustrative embodiment, the open loop system is configured such that the first set of pumps, pumps A 103 and B 104, source respective mobile phases which produce the solvent gradient composition through the chromatographic column 109, thereby causing elution of analytes from the column. In reverse phase HPLC, these mobile phases may comprise water and acetonitrile. In LC-NMR applications where proton-NMR spectroscopy is being performed, the mobile phases may comprise the deuterated forms of the respective solvents, namely D20 and deuterated acetonitrile, the usage of which dramatically reduces the background signal derived from solvent protons. In the illustrative embodiment, the mobile phases delivered by pump A 103 and pump B 104 are the aqueous phase and the organic phase, respectively. The second set of pumps, pump C 105 and D 106 in the illustrative embodiment are used to source the identical phases as pump A 103 and pump B 104, respectively. Pump A 103 and pump C 105 may share or draw from a common mobile phase reservoir, and pump B 104 and pump D 106 may share or draw from a common reservoir. The pumps may be constructed in the manner specified in U.S. Pat. No. 5,637,208 to Dourdeville, which is incorporated herein by reference, or they may be constructed in alternative forms known to those skill in the art.

During gradient elution, a time-varying solvent composition is applied to the column 109, typically resulting in a solvent mixture which varies from a lower solvating capability to a higher solvating capability throughout the analysis. In the illustrative embodiment, when using reverse-phase HPLC, the lower solvating capability corresponds to a high percentage of the aqueous component. As the gradient progresses, the percentage of the aqueous component is reduced, and the percentage of the organic component is increased in a complementary fashion. In the "high-pressure gradient formation" architecture shown, the percentage of the respective components in the solvent blend is controlled by varying the flow rates of the respective pump A 103 and pump B 104. In the illustrative embodiment, the flow rates of the individual pumps 103, 104, 105, 106 are dictated by the motor step rates assigned to the actuating step motors of the delivering syringe units comprising the pumps. The motor step rates of two or more pumps can be individually assigned in such a way that the sum of the output flow rates is a constant, or is a time-varying value which changes in accordance with a program assigned by the user.

In the common case of a compositional gradient conducted at a fixed total flow rate, the change in pump flow rate of pump A 103 is complemented by the change in pump flow rate of pump B 104, such that the solvent composition is changed while the total flow rate is held constant.

This situation can be reflected algebraically by the following simple expressions:

$$A=(a/100)*F$$

$$B=(b/100)*F=((100-a)/100)*F=F-A$$

where a=requested per cent of aqueous component in the solvent mixture; and $$0<=a<=100;$$

b=requested per cent of organic component in the solvent mixture; and $$0<=b<=100;$$

a+b=100 by definition, for binary gradient;
F=requested total chromatographic flow rate through column;
A=instantaneous flow rate of pump A 103; and
B=instantaneous flow rate of pump B 104.

During gradient elution, this calculation is performed at each of many time points, where the requested percentage of the aqueous and organic components is updated to correspond with a user-defined profile.

In the illustrative embodiment, the solvent delivered by pumps C 105 and D 106 is summed with the solvent delivered by pump A 103 and pump B 104 at the nano-volume tee 113, to produce the final composition delivered to the downstream components such as the NMR detection cell 114. Introduction of solvent downstream of the chromatographic column 109 makes it possible to substantially decouple the solvent changes required for chromatographic separation at the column 109 from the solvent environment where NMR detection occurs 114.

In the illustrative embodiment, pump A 103 and pump B 104 deliver complementary flow rates, such that the sum of their output flow rates is a constant, throughout the chromatographic analysis. Pump C 105 and pump D 106 also deliver complementary flow rates, such that the sum of their output flow rates is also constant, and is substantially identical to the total flow rate delivered by pump A 103 and pump B 104. If the controller 100 assigns identical flow rates to pump A 103 and pump D 106, and similarly assigns identical flow rates to pump B 104 and pump C 105, it will be seen that the resulting composition delivered to the components downstream of the nano-volume tee 113 including the NMR detection cell 114, remains substantially constant at 50:50 aqueous:organic. This composition is delivered at a flow rate which is also substantially constant, at a value which is twice the chromatographic flow rate.

This situation can be reflected algebraically by the following simple expressions:

$$D=(a/100)*F=A;$$

$$C=(b/100)*F=((100-a)/100)*F=B;$$

where C=instantaneous flow rate of pump C 105;
D=instantaneous flow rate of pump D 106; and
The total post-column addition flow rate is, PostColumnFlow=D+C=A+B=F. Of the total flow being sourced to the NMR cell, the flow rate of the organic component is, $$OrganicFlow=B+D=[(((100-a)/100)*F)+((a/100)*F)]=F$$

Correspondingly, the flow rate of the aqueous component sourced to the NMR cell is, $$AqueousFlow=A+C=[((a/100)*F)+(((100-a)/100)*F)]=F$$

Therefore the total overall flow sourced to the NMR cell is, $$TotalFlow=OrganicFlow+AqueousFlow=2F.$$

The situation can be generalized for gradients involving n mobile phase components. Each of the n components will have an associated column flow contribution $Flow_{column}$ and post-column flow contribution Flow$_{post\text{-}column}$. The sum of the column flow and post-column flow for any mobile phase component Flow$_{component\ total}$ will be set equal to the chromatographic flow rate. Each of the n component flows will represent 1/n of the total flow arriving at the NMR detection cell. The composition contribution, as seen at the NMR cell, of each of the n mobile phase components will therefore remain fixed at 100/n per cent.

Algebraically, if a is the instantaneous called-for percentage of a given solvent component G in a chromatographic solvent mixture comprising n solvent components, and if the mixture is flowing through a column at an instantaneous flow rate F, to bring about chromatographic elution, then:

$$FlowG_{column} = (a/100)*F;$$

$$FlowG_{post\text{-}column} = ((100-a)/100)*F;\ \text{and}$$

$$FlowG_{component\ total} = FlowG_{column} + FlowG_{post\text{-}column} = [((a/100)*F) + (((100-a)/100)*F)] = F$$

The above calculation can be performed for each of the n components of the chromatographic mobile phase. The total flow (the sum of the chromatographic and compensation flows) appearing at the NMR detection cell is:

$$n*F$$

The compositional contribution of any single mobile phase component at the NMR detection cell, expressed as a percentage, is given by:

$$(F/(n*F))*100 = (1/n)*100 = 100/n$$

In the illustrative embodiment, solvent compositions formed by pump A 103 and pump B 104 are delivered to the nano-volume tee 113 after a volume delay which is related to the volumes of the in-line components which must be traversed, including the sample injection valve 107, the column 109, the in-line chromatographic detector 111 and the plurality of interconnecting tubing. Because of the manner in which these various geometries are swept by the fluid stream, the solvent gradient will be subject to both a delay in time, and to some loss of fidelity in shape, due to parasitic mixing processes. Therefore, if the solvent mixture provided by pump A 103 and pump B 104 is to be substantially compensated, from a compositional standpoint, by the mixture provided by pump C 105 and pump D 106, then in the illustrative embodiment, it will be necessary to cause the pump C 105 and pump D 106 mixture to traverse an analogous sequence of fluidic elements. These fluidic elements are approximately representative of the chromatographic counterparts with regard to the disposition of volume, and ideally with regard to resistance to flow, though they need not embody all of the complexity of the chromatographic components they are configured to mimic. As shown in FIG. 1, volume 1 108 mimics the fluidic properties of the injector 107. The fluidic properties of the column 109 are duplicated by the resistance 110 and the fluidic properties of the flow cell 111 are duplicated by the volume 112. The fluidic properties of the plurality of connecting tubes within the A/B or analytical pathway are duplicated by similar fluidic connections within the C/D or compensation pathway.

The open-loop method shown in the illustrative embodiment does not require an additional fluid composition sensing cell or active feedback loop. However, it may be desirable, in analyses where there is a rapid rate-of-change of solvent composition requested by the user, to employ a configuration which utilizes an active feedback system for solvent composition compensation.

Figure 2:
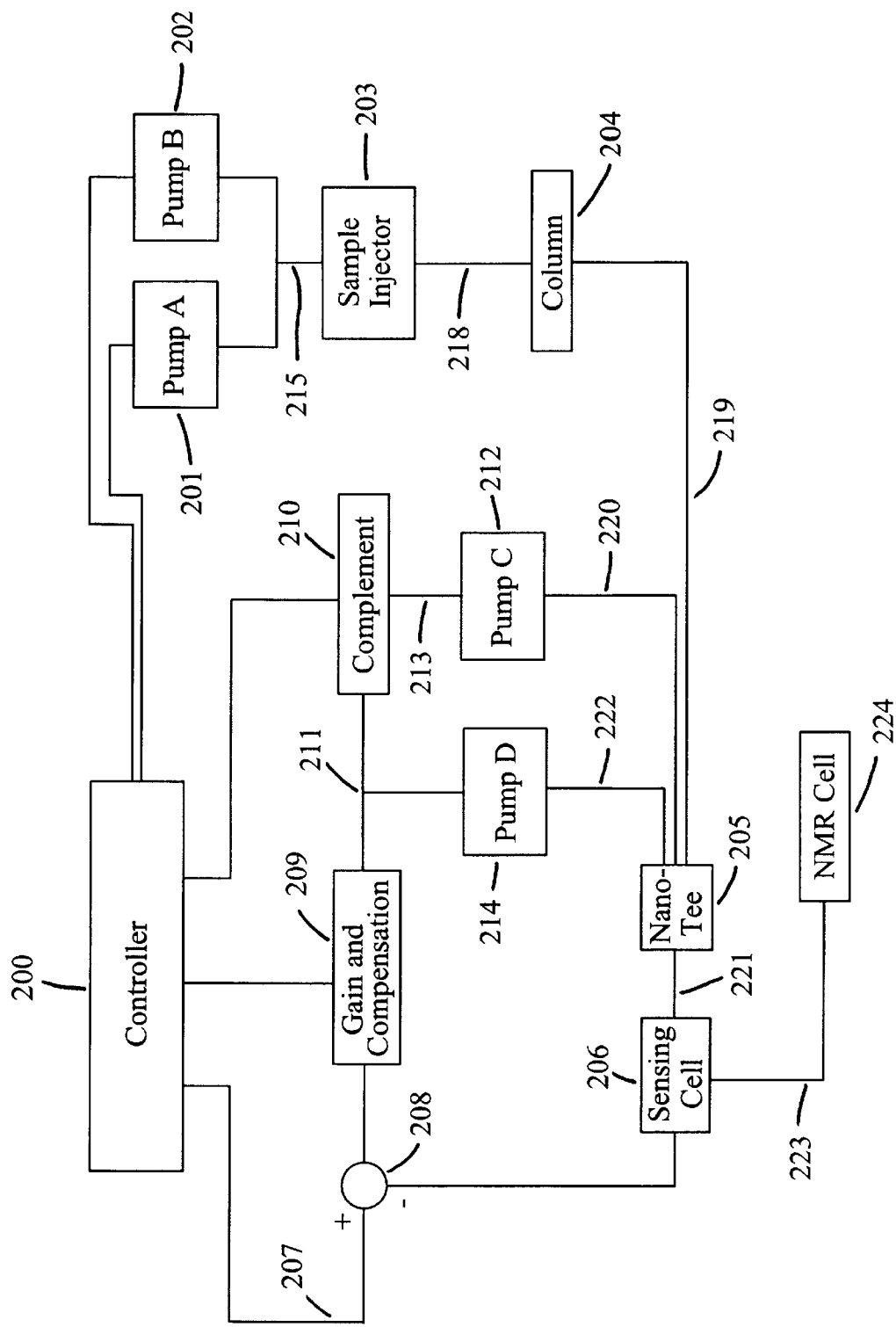
FIG. 2 shows a schematic drawing of a feedback or closed-loop system of the present invention.

Referring to FIG. 2, an alternative embodiment of the present invention is shown. This illustrative embodiment accomplishes solvent composition compensation by employing an active feedback system. This alternative embodiment, having active feedback, comprises a system controller 200. The system controller 200 is in communication with a first pump A 201 and a second pump B 202. Pump A 201 and pump B 202 are configured to deliver an aqueous and an organic mobile phase, respectively. The first pump A 201 and the second pump B 202 have connecting tubes 215. The connecting tubes 215 cause the first pump A 201 and the second pump B 202 to be in mutual fluidic communication with a sample injector 203. The sample injector 203 has a connecting tube 218 that causes the sample injector 203 to be in fluidic communication with a chromatography column 204. The chromatography column has a connecting tube 219 connecting the chromatography column 204 in fluidic communication with a downstream nano-volume tee 205. These components of the alternative embodiment are similar to those employed within the A/B fluidic path of the open loop system shown in FIG. 1. At the option of the user, an in-line chromatographic detector may be interposed at a location of choice in the analytical fluid path.

In this alternative embodiment, the fluidic properties of the secondary, or compensating, mobile phase pathway are configured for use in a feedback mode. The closed-loop mode of operation eliminates the need, defined for the open loop embodiment, for matching the fluidic circuit of the analytical pathway with analogous fluidic components in the secondary, or compensating, fluid pathway. The system controller 200 is in communication with a pump C 212. The pump C 212 has a connecting tube 220 that causes the pump C 212 to be in fluidic communication with the nano-volume tee 205. The system controller 200 also is in communication with a pump D 214. The pump D 214 has a connecting tube 222 connecting the pump D 214 in fluid communication with the nano-volume tee 205.

Pump C 212 and pump D 214 are configured to deliver an aqueous and an organic mobile phase, respectively. Pump C 212 may draw from the same solvent reservoir as pump A 201, and pump D 214 may draw from the same solvent reservoir as pump B 202. The nano-volume tee 205 has a connecting tube 221 that causes the nano-volume tee 205 to be in fluidic communication with a sensing cell 206. The sensing cell 206 is configured to detect a property of the combined mobile phase arriving at the sensing cell 206 by way of the nano-volume tee 205. In the illustrative embodiment, the sensing cell 206 is configured to measure a property of the mobile phase which is correlated to the mobile phase composition. The sensing cell 206 is in communication with the controller 200, as part of a configured feedback loop.

In this illustrative embodiment, the controller 200 assigns respective flow rates to pump A 201 and B 202 in accordance with a method specified by the user, so as to bring about the user's intended profile of solvent composition and solvent flow rate as a function of time throughout a given analysis. It will be noted that a compositional change may be effected with or without a change to the total flow rate assigned to the pump A 201 and pump B 202 pair. As that time-programmed method is being executed, the controller operates pump C 212 and pump D 214 as part of a feedback loop responsive to the output signaled by sensing cell 206.

The feedback loop includes a reference set-point input 207, an error detection function 208, a gain and frequency compensation function 209, and a flow rate complementing function 210. The error detection function 208, gain and frequency compensation function 209, and flow complementing function 210 may be implemented in hardware or software or a combination of the two, as suits the application. The flow complementing function 210 accepts as input the commanded flow rate 211 for pump D 214, and produces from that the corresponding commanded flow rate 213 which is assigned to pump C 212. In executing the feedback loop, the controller assigns respective flow rates to pump C 212 and pump D 214 in order to null any measured deviation of the sensing cell 206 output from the reference set-point input 207. The controller computes the respective flow rate outputs of pump C 212 and pump D 214 to be complementary, where the sum of the pump C 212 and pump D 214 flow rates is held equal to the sum of the pump A 201 and pump B 202 flow rates, independent of the instantaneous composition being demanded from the pump C 212 and pump D214 pair.

The function of the feedback loop is such that a compositional error arising in the instantaneous solvent composition detected at sensing cell 206, indicative of a composition deficient in the organic component, will bring about an increase in the flow rate of pump D 214, and a corresponding decrease in the flow rate of pump C 212, in accordance with error detection, gain, and frequency compensation calculations as are known in the art. Thus the system controller 200 modulates the compositional delivery of the pump C 212 and pump D 214 pair so as to actively maintain the solvent composition measured at sensing cell 206 substantially constant. In so doing, the controller 200 attempts to null the difference between the measured solvent composition and the reference setpoint. The controller 200 also ensures that the sum of the flow rates delivered from the compensation pump pair C 212 and D 214 is equal to the sum of the flow rates of the analytical pump pair A 201 and B 202.

In the alternative embodiment, solvent composition sensing is performed at the dedicated sensing cell 206. The summing point for the fluidic streams is configured as a four-port, nano-volume tee 205, as shown in FIG. 2. The implementation of the tee function may be accomplished discrete from the sensing cell 206, or may be incorporated into the sensing cell 206 structure. In either case, sensing cell 206 incorporates a connecting tube 223 which causes the sensing cell 206 to be in fluid communication with the NMR detection cell 224.

While the magnetic susceptibility of the fluid stream might be measured directly, and thus controlled, it also possible to measure another attribute of the stream, such as the solvent composition, and use that measurement as the basis of control for compensation purposes. Absorbance-based spectroscopic measurements such as infra red (IR) or ultraviolet (UV) absorbance, dielectrometry, conductivity, and refractometry comprise viable candidates for this sensing function, and are well known in the art. Since the solvent composition control will be exercised around a specified operating point, it is not necessary that the measurement be linear throughout the entire compositional range, nor even monotonic throughout the entire range. Rather, it is desirable to have the measurement be monotonic, and ideally reasonably linear, within a limited range bracketing the operating point.

Although the open loop method of solvent compensation described in the illustrative embodiment herein matches or mimics the fluidic characteristics of the analytical fluid pathway by incorporating two discrete matching volumes, a discrete matching resistance, and associated connecting tubing within the compensation fluid pathway, it should be appreciated by those skilled in the art that a single element or a plurality of elements could be incorporated into the compensation fluid pathway for the purpose of matching the fluidic characteristics of any combination of elements transited by the analytical fluid stream.

Although the solvent compensation described in the illustrative embodiments is presented in the context of coupling liquid chromatography with NMR spectroscopy, it should be appreciated by those skilled in the art that the compensation strategy is equally applicable to the coupling of other liquid-phase analysis techniques such as gradient-mode capillary electrochromatography (CEC) with NMR spectroscopy.

Although the illustrative examples show the incorporation of an in-line chromatographic detector which is auxiliary to the NMR spectrometer, it should be appreciated by those skilled in the art that the inclusion of one or more in-line chromatographic detectors is at the option of the user, depending upon the nature of the data required, and that these in-line detectors may be deployed upstream or downstream of the point where the analytical and the compensation flows converge.

Although the illustrative example depicting closed-loop compensation shows a chromatographic detector which is separate from the solvent property sensing cell, it should be appreciated that a single detector and flow cell could be constructed which performs the functions of both chromatographic detection and solvent property sensing. An example of this would be the use of simultaneous multiple-wavelength photodiode array detection for ultraviolet (UV) absorbance measurement, where chromatographic peak detection is performed in a region of the UV spectrum where the solvents are substantially transparent, and where the solvent composition detection is performed in a region of the spectrum where one solvent component has a significant UV absorbance, and the other solvent component does not.

While the illustrative example depicting open-loop compensation shows separate and independently-motorized pumps A, B, C and D, it should be appreciated that in a system dedicated for this purpose, the syringes for pumps A and D could be driven by a common linear translation mechanism, and the syringes for pumps B and C could be driven by a common linear translation mechanism, such that very precise matching of the formed complementary gradients could be accomplished.

Similarly, although the illustrative examples depict solvent gradient generation using a high-pressure gradient formation architecture, and employing pumps which are constructed on a syringe principle, it should be recognized by those skilled in the art, that solvent gradients can also be generated using a low-pressure proportioning principle, where solvent composition is controlled at the inlet or low-pressure side of a given pump, typically using selectable solvent switching valves, and that the pumps may be constructed as diaphragm pumps, peristaltic pumps, electrokinetic pumps, or other geometries as suit the application.

Although the illustrative examples depict a binary or two-component compositional gradient being applied to a liquid chromatography column, and a binary or two-component flow summed with the chromatographic flow post-column for the purpose of compensation, it should be recognized by those skilled in the art that ternary or higher-order solvent mixtures can be compensated by the present method. Moreover, it should be further recognized that it is not a requirement that the post-column or compensation flow rate be maintained at a value identical to the column flow rate. Particularly where a binary analytical solvent variation encompasses a relatively narrow range (for example, from 10 to 20 per cent change in composition), and where the total flow rate provided to the NMR spectrometer need not remain fixed, solvent compensation can be performed by the variable addition of a single solvent component, thereby maintaining a specified composition, susceptibility, or other solvent property constant throughout the analysis.

Although the illustrative examples are developed around compensation or stabilization of a solvent composition, thereby achieving stabilization of other correlated solvent properties such as density, viscosity, dielectric constant, or magnetic susceptibility, it should be recognized by those skilled in the art that the present method could be employed in the compensation or stabilization of any particular solvent property for which a measurement is directly obtainable, or which can be inferred by relationship to another solvent property which is measurable. The compensating flow may comprise solvents which are the same solvents as are used in the analytical flow, delivered in complementary or otherwise varying amounts. Alternately, the compensating flow may comprise one or more unique solvents, the addition of which results in the modulation of a property of interest for the combined stream delivered to the NMR detection cell. The compensating solvent may comprise a pure solvent, or may comprise a solvent in combination with additives, the use of which modifies a solvent property of interest.

The foregoing has been a description of illustrative embodiments of the present invention. The present invention is not to be limited in scope by the illustrative embodiments described which are intended as specific illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

What is claimed is:

1. An apparatus for limiting the variation in magnetic susceptibility of a liquid stream delivered to a nuclear magnetic resonance based detector, comprising:
    a system controller in communication with a first fluid stream, said first fluid stream having a first magnetic susceptibility; and
    said system controller in communication with at least one additional fluid stream, said at least one additional fluid stream having a differing magnetic susceptibility;
    wherein said at least one additional fluid stream is summed with said first fluid stream to compensate for the variation in magnetic susceptibility of said first fluid stream.

2. An apparatus for limiting the variation in magnetic susceptibility of a liquid stream delivered to a nuclear magnetic resonance detector comprising:
    a system controller being in communication with a first fluid stream having a first magnetic susceptibility;
    said system controller in communication with at least one additional fluid stream having a differing magnetic susceptibility;
    a first set of pumps conveying fluid within said first fluid stream; and
    an additional set of pumps conveying fluid within each said at least one additional fluid stream;
    wherein said first set of pumps creates said first fluid stream having a time varying magnetic susceptibility and where said additional set of pumps creates said at least one additional fluid stream having a time varying magnetic susceptibility which is complementary to that of said first fluid stream.

3. The apparatus of claim 2 further including a sample injector within said first fluid stream.

4. The apparatus of claim 2 further including a column within said first fluid stream.

5. The apparatus of claim 2 further including an detector within said first fluid stream.

6. The apparatus of claim 2 further including a fluid junction, wherein said first fluid stream and said at least one additional fluid stream are joined forming an output stream.

7. The apparatus of claim 6 wherein said system controller senses a property of said output stream and modulates said at least one additional stream to maintain a magnetic susceptibility of said output stream constant.

8. The apparatus of claim 2 further including a first volume, a second volume and a resistance within said additional fluid stream.

9. The apparatus of claim 8 wherein said first volume, said second volume and said resistance are contained within one element.

10. The apparatus of claim 8, wherein said first volume, said second volume and said resistance mimic properties of components of said first fluid stream.

11. The apparatus of claim 2, wherein said first set of pumps contain a first pump and a second pump and said additional set of pumps contain a first pump and a second pump.

12. The apparatus of claim 11, wherein said pumps are syringe pumps.

13. The apparatus of claim 12 wherein said pumps are driven by a common linear translation mechanism.

14. The apparatus of claim 11, wherein said pumps are diaphragm pumps.

15. The apparatus of claim 11, wherein said pumps are peristaltic pumps.

16. A method for compensation of magnetic susceptibility variation in a fluid stream directed to a nuclear magnetic resonance detection device, comprising the steps of:
    forming a first fluid stream having a first magnetic susceptibility;
    forming at least one additional fluid stream having a differing magnetic susceptibility;
    summing said first fluid stream into said at least one additional fluid stream, and forming an output stream; and
    modulating said at least one additional fluid stream to maintain a magnetic susceptibility of said output stream constant.

17. The method of claim 16, further including the step of sensing a property of said output stream which is correlated to the magnetic susceptibility of said output stream.

18. The method of claim 16, wherein said first fluid stream and said at least one additional fluid stream are configured as an open-loop system and a time-programmed gradient is executed substantially simultaneously by a multiple solvent gradient generation system.

19. The method of claim 17, wherein said first fluid stream and said at least one additional fluid stream are configured as a closed-loop system and a controller actively senses a property of said output stream and said controller modulates output of said at least one additional fluid stream in order to maintain constant said property of said output stream.

* * * * *